United States Patent
Siciliano et al.

(10) Patent No.: US 12,415,062 B2
(45) Date of Patent: Sep. 16, 2025

(54) SWITCH FOR TATTOO MACHINE

(71) Applicant: FK Irons Inc., Doral, FL (US)

(72) Inventors: Gaston Siciliano, Doral, FL (US);
Christian Bonomo, Doral, FL (US);
Adriano Mendoza, Doral, FL (US);
Juan Martino, Doral, FL (US);
Roberto Hernandez, Doral, FL (US);
Omar Sanchez, Doral, FL (US);
Fernando Diaz, Doral, FL (US)

(73) Assignee: FK Irons Inc., Doral, FL (US)

( * ) Notice: Subject to any disclaimer, the term of this patent is extended or adjusted under 35 U.S.C. 154(b) by 581 days.

(21) Appl. No.: 17/670,271

(22) Filed: Feb. 11, 2022

(65) Prior Publication Data

US 2022/0257917 A1   Aug. 18, 2022

Related U.S. Application Data

(60) Provisional application No. 63/149,036, filed on Feb. 12, 2021.

(51) Int. Cl.
*A61M 37/00* (2006.01)
*H01H 13/04* (2006.01)
*H01H 13/14* (2006.01)

(52) U.S. Cl.
CPC ........ *A61M 37/0084* (2013.01); *H01H 13/04* (2013.01); *H01H 13/14* (2013.01);
(Continued)

(58) Field of Classification Search
CPC .... Y10T 74/20888; A61B 2017/00221; A61B 2017/00973; A61B 90/08; H01H 3/14;
(Continued)

(56) References Cited

U.S. PATENT DOCUMENTS 5,968,063 A * 10/1999 Chu ................. A61H 39/08
606/189
6,898,525 B1   5/2005 Minelli
(Continued)

FOREIGN PATENT DOCUMENTS

DE   3827064 A1   2/1990

OTHER PUBLICATIONS

PCT International Search Report for PCT Application No. 22/16215, dated May 11, 2022.

*Primary Examiner* — Anthony R Jimenez
(74) *Attorney, Agent, or Firm* — Akerman LLP; Peter A. Chiabotti

(57) ABSTRACT

A switch or footswitch for use with a tattoo machine is disclosed. The switch or footswitch may include a housing configured to protect and house a plurality of components of the switch or footswitch. The housing may include an accelerometer that may be utilized to detect an acceleration associated with the switch or footswitch, such as a tap made on the housing itself. Upon detection of an acceleration associated with the switch or footswitch, the accelerometer may generate a signal and transmit the signal to a communication device of the switch or footswitch. The communication device may then transmit the signal to the tattoo machine to activate the tattoo machine, deactivate the tattoo machine, adjust a setting of the tattoo machine, or control operative functionality of the tattoo machine. The switch or footswitch may also include a radio frequency ground plate and overlay membrane to enhance radio frequency reception.

19 Claims, 18 Drawing Sheets

(52) U.S. Cl.
CPC ............... *A61M 2205/3327* (2013.01); *A61M 2205/3561* (2013.01); *A61M 2205/8206* (2013.01)

(58) Field of Classification Search
CPC .... H01H 1621/26; H01H 13/00; H01H 13/04; H01H 13/14; G05G 1/30; G06F 3/0346; G06F 1/625; G08C 17/02; A61M 37/00; A61M 37/0076; H04B 1/02; H04B 1/06
USPC ........................................................ 200/86.5
See application file for complete search history.

(56) References Cited

U.S. PATENT DOCUMENTS

| | | |
|---|---|---|
| 2004/0233172 A1 | 11/2004 | Schneider et al. |
| 2011/0288575 A1 | 11/2011 | Colton et al. |
| 2012/0188004 A1 | 7/2012 | Slotznick |
| 2015/0014214 A1 | 1/2015 | Richardson |
| 2017/0187422 A1 | 6/2017 | Hosseini et al. |
| 2019/0113961 A1 | 4/2019 | Iyer et al. |

* cited by examiner

SWITCH FOR TATTOO MACHINE

CROSS REFERENCE TO RELATED APPLICATIONS

This application claims priority to and the benefit of U.S. Provisional Patent Application No. 63/149,036, filed on Feb. 12, 2021, which is hereby incorporated by reference in its entirety.

FIELD OF THE APPLICATION

The present application relates to tattoo machines, switches and footswitch devices, control devices, communication devices, communication technologies, and, more particularly, to a switch and footswitch for use with a tattoo machine.

BACKGROUND

Currently, the tattoo industry has become increasingly popular around the world and the demand for tattoos has increased exponentially. In order to meet the rapidly rising demand for tattoos, tattoo-related businesses are actively searching for ways in which to optimize the process entire tattooing process. To that end, businesses have spent significant financial resources towards developing technologically advanced tattoo machines, sanitation technologies, tattoo-machine accessories, and the like. For example, tattoo machines have been developed that enable tattoo artists to adjust the voltage delivered to the motor of a tattoo machine with the press of a button, a voice command, or through or input mechanisms to adjust the reciprocation of needles of the tattoo machines. Additionally, tattoo machines have been developed to be more ergonomic and user-friendly for tattoo artists so that tattoo artists can tattoo for longer periods of time. Furthermore, tattoo machine accessories have been developed to not only enhance the functionality of tattoo machines, but to also help to make the tattoo machines easier to use. Such accessories include, but are not limited to, grips, needle cartridges, housings, battery packs, among other accessories. Nevertheless, currently existing tattoo machines and tattoo machine accessories still do not provide all of the desired functionality and features needed by the tattoo industry.

Based on at least the foregoing, there is room for significantly enhancing tattoo machine technologies and related accessories, such as footswitches. Currently existing technologies often have numerous wires or cables that interfere with a tattoo artists mobility, freedom, and/or tattooing dexterity. Additionally, currently existing footswitch technologies require a user to depress a mechanical switch to adjust the circuit state of a footswitch. Based on at least the foregoing, current tattoo machines and accessories may be improved and enhanced so as to provide for improved modularity, increased mobility for tattoo artists, enhanced methods of tattoo machine activation or deactivation, and enhanced methods for controlling tattoo machines. Such enhancements and improvements to methodologies and technologies may provide for increased tattoo artist productivity, enhanced functionality, and greater versatility.

SUMMARY

A switch or footswitch for use with a tattoo machine and accompanying methods for utilizing the footswitch are disclosed. The footswitch may be utilized to activate and control a tattoo machine without the use of a user's hands, without an abundance of cables that may get in a tattoo artist's way, and without having to use a mechanical switch to change the circuit state when activated. The footswitch may eliminate the need for a mechanical switch and may allow for activation of the footswitch and/or a tattoo machine from any direction with respect to the housing and/or chassis of the footswitch. In particular, the footswitch may be a solid-state footswitch that includes an accelerometer and/or other sensors that may be utilized to activate, deactivate, and/or control the functionality of the footswitch. When an acceleration associated with the footswitch is detected by the accelerometer of the footswitch, the accelerometer may transmit a signal to a communication device of the footswitch, which may then wirelessly transmit the signal to a communication device or other component of a communicatively linked tattoo machine. The signal may be utilized to activate the tattoo machine, deactivate the tattoo machine, control the tattoo machine, adjust a setting of the tattoo machine, or a combination thereof.

In one embodiment, a tattoo machine system including a tattoo machine and an accompanying footswitch is provided. The tattoo machine system may include a tattoo machine, which may be utilized by a tattoo artist to apply tattoo ink to the skin of a user. The tattoo machine system may also include a footswitch configured to communicatively link with the tattoo machine. The footswitch may include a housing. In certain embodiments, the housing may be made of plastic using overmolded rubber to protect the interior hardware of the footswitch from impact and/or intrusion by substances. In certain embodiments, the housing may also include a plug for sealing a top portion of the exterior of the housing to prevent agents or liquids from entering the interior of the footswitch. In certain embodiments, the housing may have a shape such that when the footswitch is lying flat on a surface, any liquids poured over the surfaces of the housing will flow away from the footswitch. The footswitch may also include an accelerometer, a communications device, a bottom lid, a radio frequency ground plate and overlay membrane, among other components. In certain embodiments, the components may reside within, on, or about the housing of the footswitch. The accelerometer of the footswitch may be configured to detect an acceleration associated with the footswitch. For example, the accelerometer may be configured to detect a tap conducted on a surface of the footswitch, such as by the foot of a user. Other motions and/or movements may be also be detected by the accelerometer. Once an acceleration is detected, the accelerometer may generate a signal and transmit the signal to the communication device of the footswitch. The communication device of the footswitch may be configured to transmit the signal received from the accelerometer to the tattoo machine, such as to a communication device of the tattoo machine. The signal may be utilized to activate the tattoo machine, deactivate the tattoo machine, control an operation of the tattoo machine, adjust a setting of the tattoo machine, perform any action with respect to the tattoo machine or a combination thereof. As additional accelerations are detected by the accelerometer, additional signals may be transmitted to the tattoo machine to perform further actions.

In another embodiment, a method for utilizing a footswitch with a tattoo machine is disclosed. The method may include positioning a footswitch within range of a tattoo machine. For example, positioning the footswitch within range of the tattoo machine may include positioning the footswitch within communication range of the tattoo machine. Additionally, the method may include monitoring for an acceleration associated with the footswitch via an accelerometer of the footswitch. For example, the accelerometer may be configured to detect an acceleration occurring on any surface of the footswitch, such as on the housing the footswitch. If an acceleration is detected, the method may include generating a signal using the accelerometer. The method may then include transmitting the signal from the accelerometer to a communication device of the footswitch. The method may proceed to include transmitting the signal from the communication device to the tattoo machine that is in range of the footswitch. The signal may be utilized to facilitate performance of an action with respect to the tattoo machine. The action, for example, may include activating the tattoo machine, deactivating the tattoo machine, controlling an operation of the tattoo machine, adjusting a setting of the tattoo machine, and/or performing any other action with respect to the tattoo machine. The method may then include continuing to monitor for additional accelerations that occur and utilized signals generated based on the additional accelerations to control the tattoo machine.

According to yet another embodiment, a footswitch for use with a tattoo machine is disclosed. The footswitch may include a housing, an accelerometer, a communication device a bottom lid, a radio frequency ground plate and overlay membrane, a battery charger circuit, a rechargeable battery, a memory, a processor, a power switch, a port, and/or any other desired components. The accelerometer, which may be positioned within the housing of the footswitch, may be configured to detect accelerations occurring on a surface of the housing of the footswitch. For example, the footswitch may detect taps on the surface, motions on the surface, slides on the surface, patterns of taps on the surface, and/or any other contacts with the surface of the footswitch. Upon detections of the accelerations, the accelerometer may generate signals, which may be provided to the communication device of the footswitch. The communication device of the footswitch may transmit the signal to a tattoo machine to facilitate performance of an action with respect to the tattoo machine. The bottom lid may be bolted to the bottom of the footswitch and the power switch for deactivating or activating the footswitch may be configured to protrude through an opening in the bottom lid. The radio frequency ground plate and overlay membrane may be affixed to a portion of the bottom lid and may be utilized to reflect radio frequency signals sent by the communication device to emit outwards in the direction of the tattoo machine instead of in an undesired direction. The battery charger circuit may be utilized to charge the rechargeable battery and regulate power for the accelerometer and the communication device. In certain embodiments, a power cable may be plugged into the port so as to provide an alternative means of power to the footswitch as well.

These and other features of the footswitch are described in the following detailed description, drawings, and appended claims.

DETAILED DESCRIPTION OF THE DRAWINGS

A switch or footswitch (e.g. footswitch 100) for use with a tattoo machine (e.g. tattoo machine 200) and accompanying methods (e.g. method 1700) for utilizing the footswitch are disclosed. The footswitch may be utilized to activate and control the tattoo machine without the use of a user's hands and without having to deal with one or more cables that may get in the way of a tattoo artist performing his or her job. In certain embodiments, the footswitch may be configured to operate without any wires having to be plugged into the footswitch itself, thereby liberating the tattoo artist from entanglement and restrictions. In certain embodiments, the footswitch may be a solid-state footswitch that includes an accelerometer and/or other sensors and components that may be utilized to activate, deactivate, and/or control the functionality of the footswitch. When an acceleration associated with the footswitch is detected by the accelerometer of the footswitch, the accelerometer may transmit a signal to a communication device of the footswitch, which may then wirelessly transmit the signal to a communication device or other component of a tattoo machine within range of the footswitch. In certain embodiments, the signal may be utilized to activate the tattoo machine, deactivate the tattoo machine, control the tattoo machine, adjust a setting of the tattoo machine, or a combination thereof.

Figure 1A:
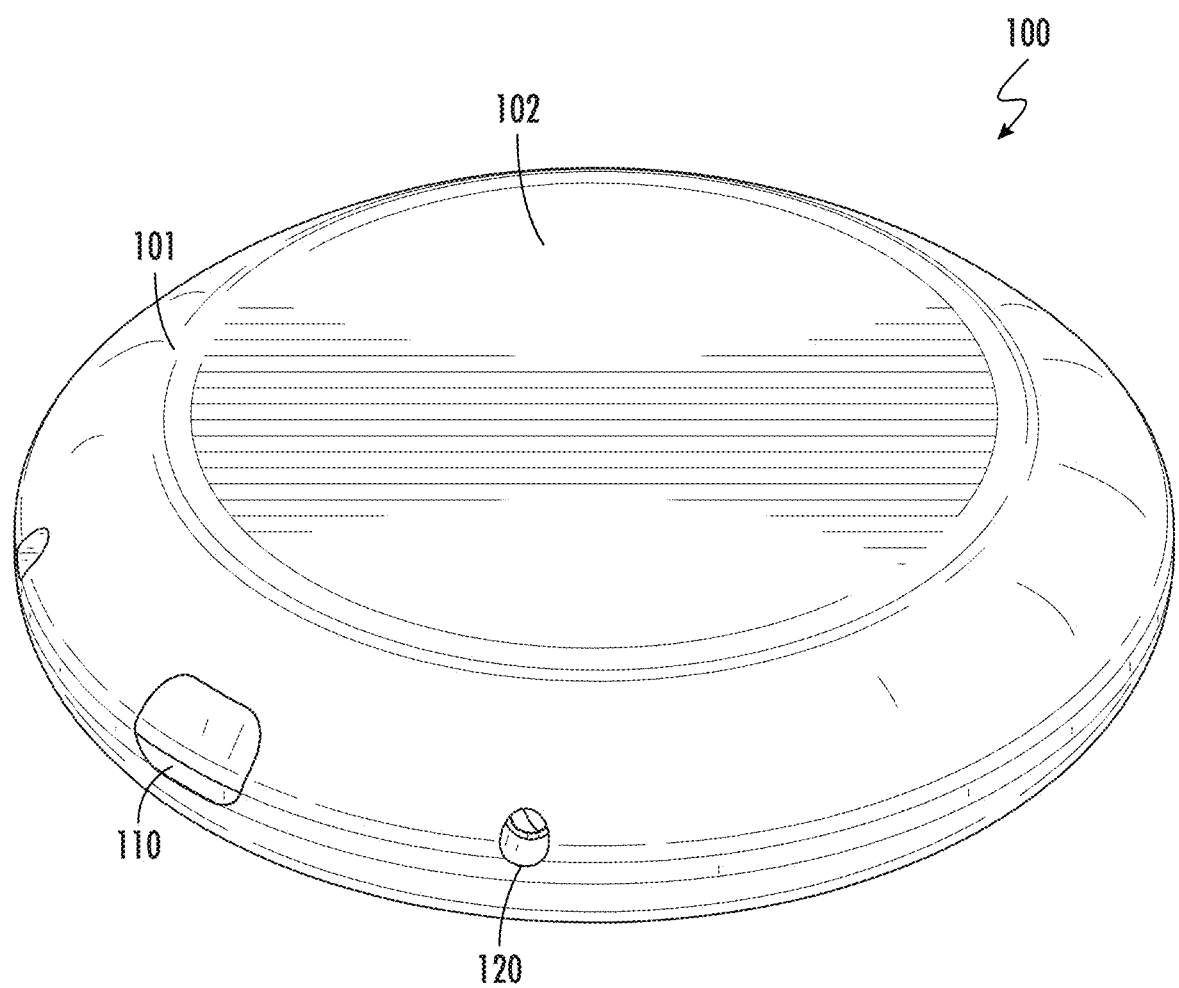
FIG. 1A is a schematic diagram illustrating a front angled perspective view of a switch or footswitch for use with a tattoo machine according to an embodiment of the present disclosure.
Figure 1B:
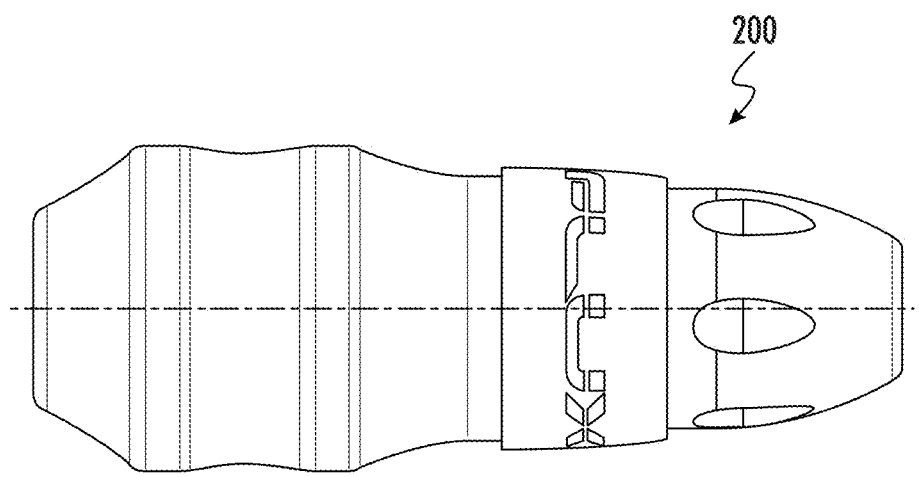
FIG. 1B is a schematic diagram of a tattoo machine for use with a switch or footswitch according to an embodiment of the present disclosure.
Figure 2:
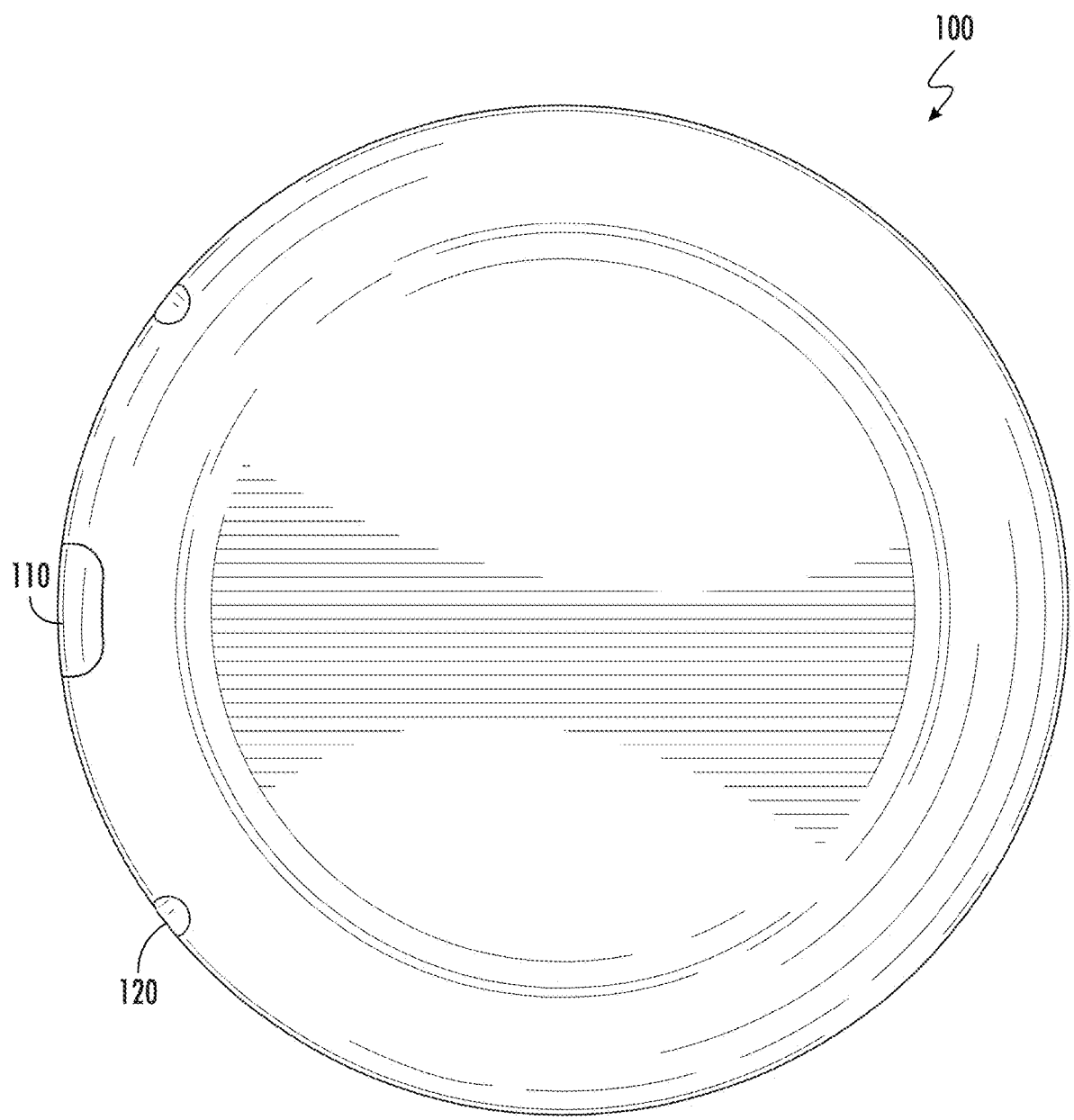
FIG. 2 is a schematic diagram illustrating a top view of the switch or footswitch of FIG. 1A.
Figure 3:
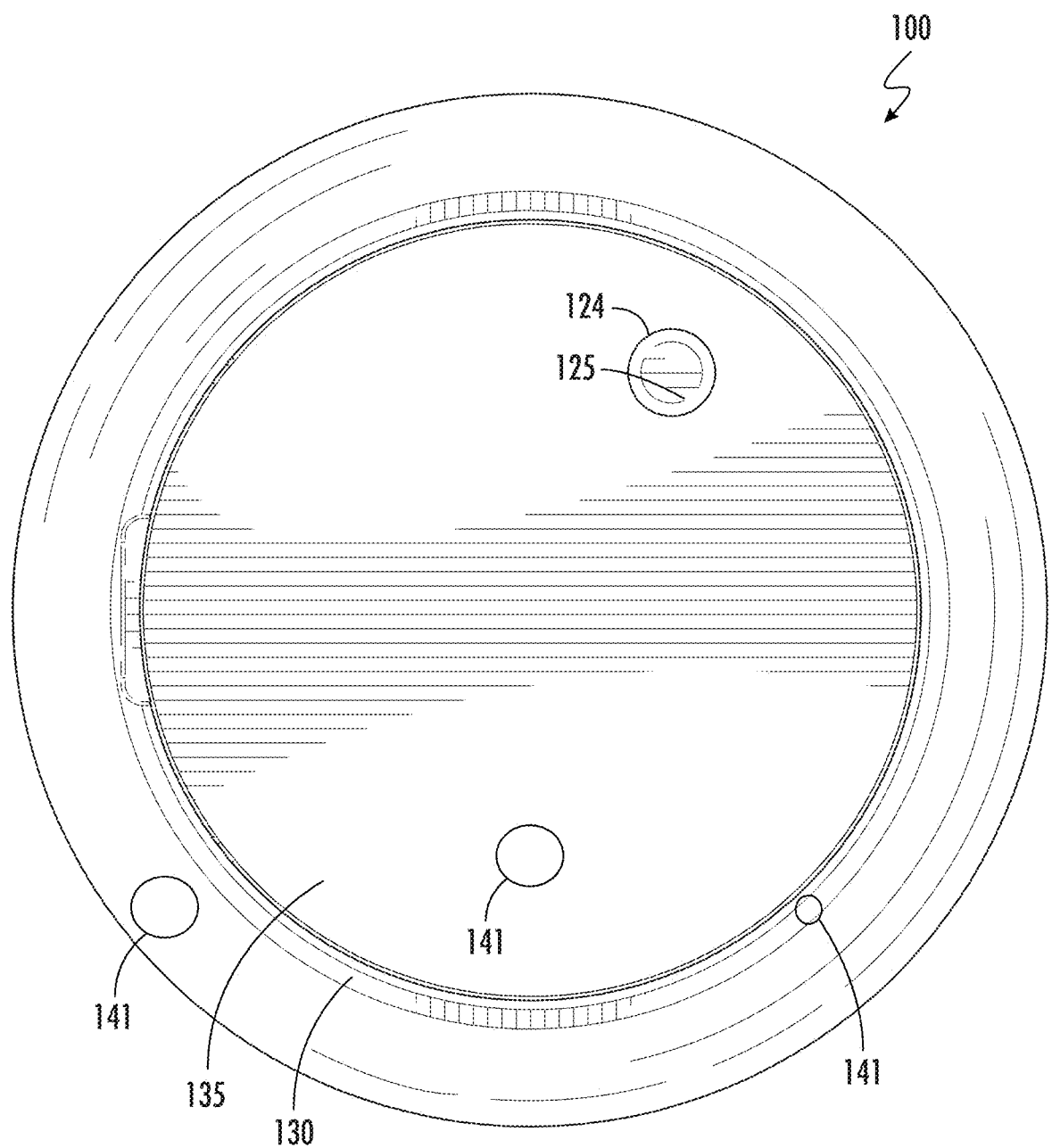
FIG. 3 is a schematic diagram illustrating a bottom view of the footswitch of FIG. 1A.
Figure 18:
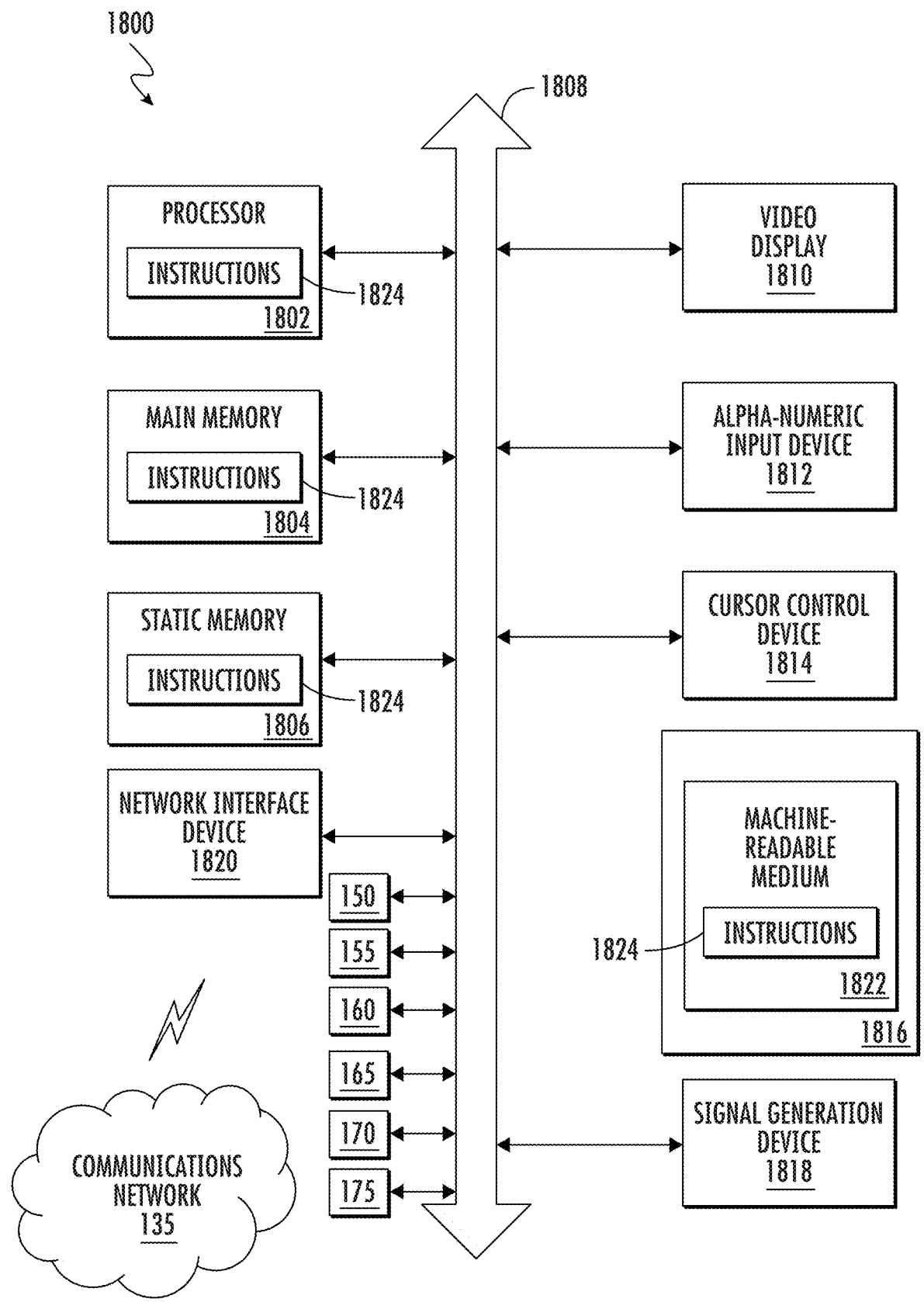
FIG. 18 is a schematic diagram of a machine that may be utilized to facilitate the operation of the footswitch and/or other devices of the present disclosure.

As shown in FIGS. 1A, 1B and referring also to FIGS. 2, 3, 4, 5, 6, 7, 8, 9, 10, 11, 12, 13, 14, 15A, 15B, 15C, 16A, 16B, 16C, 16D, 16E, and 16F, embodiments of a footswitch 100 and accompanying tattoo machine 200 are disclosed. The footswitch 100 may serve as an accessory to the tattoo machine 200 and may be utilized to control various operations of the tattoo machine 200 in response to detected accelerations associated with the footswitch 100. For example, the footswitch 100 may be operated by a user's foot so that the user's hands and attention may be directed to applying a tattoo onto the skin of a tattoo recipient. In certain embodiments, the footswitch 100 may include any number of desired components, such as, but not limited to, a housing 101, a tab 110, a port 115, vents 120, a bottom lid or plate 135, a radio frequency ground plate and overlay membrane 140, an accelerometer 150, a communication device 155, a battery 160, a battery charger circuit 165, processor 170, a memory 175, a transceiver, or a combination thereof. In certain embodiments, the footswitch 100 may include any number of sensors including, but not limited to, motion sensors, light sensors, pressure sensors, humidity sensors, temperature sensors, audio sensors, cameras, any type of sensor, or a combination thereof. In certain embodiments, the footswitch 100 may include any of the components of the machine as shown in FIG. 18 as well.

Figure 4:
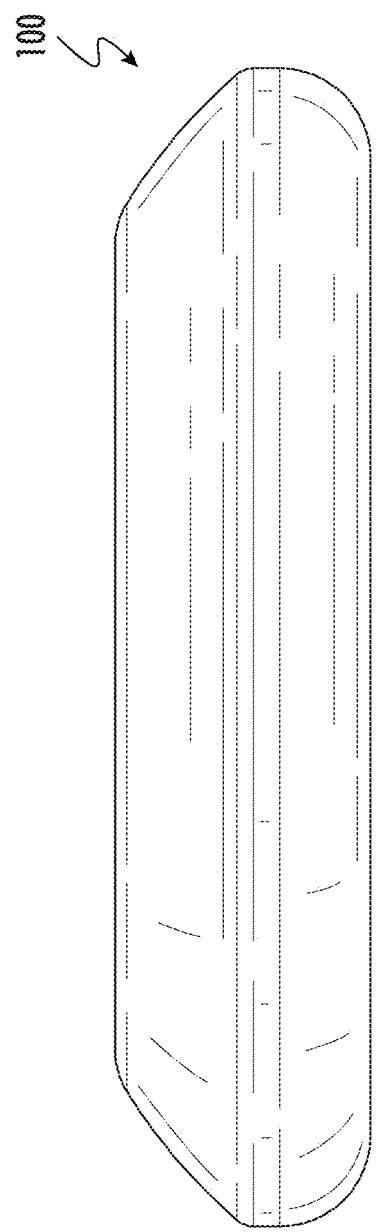
FIG. 4 is a schematic diagram illustrating a side view of the footswitch of FIG. 1A.
Figure 5:
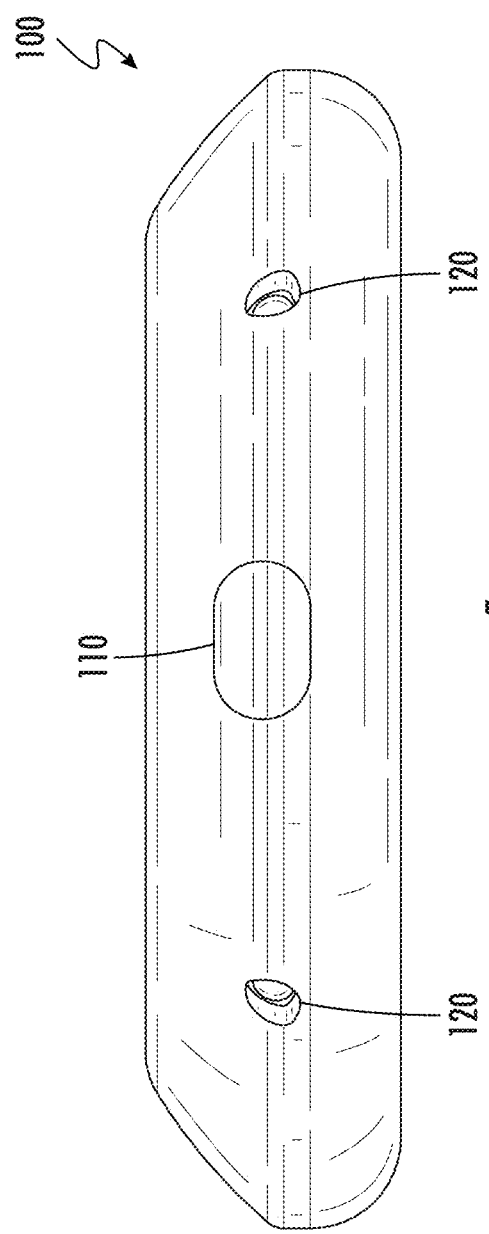
FIG. 5 is a schematic diagram illustrating another side view of the footswitch of FIG. 1A.
Figure 6:
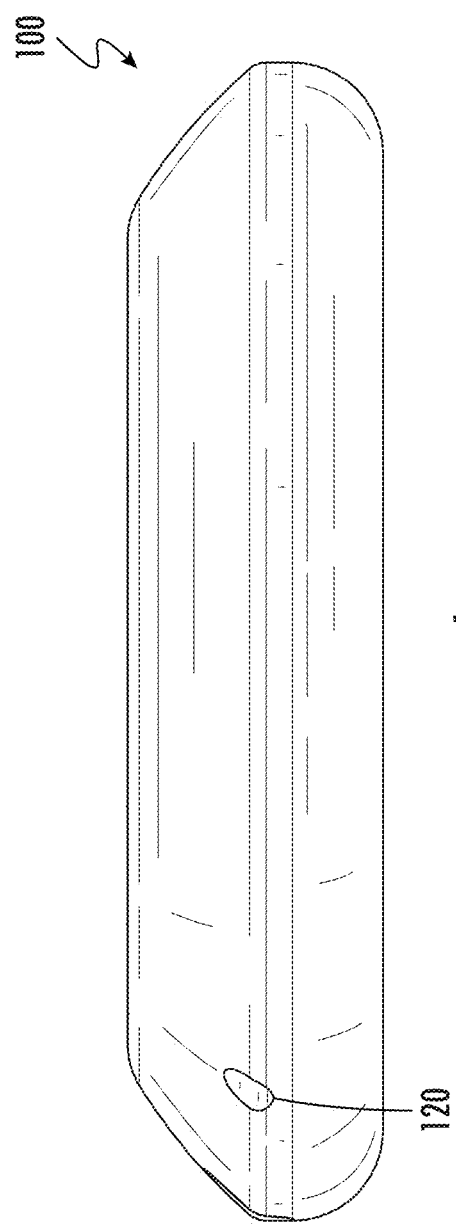
FIG. 6 is a schematic diagram illustrating another side view of the footswitch of FIG. 1A.
Figure 7:
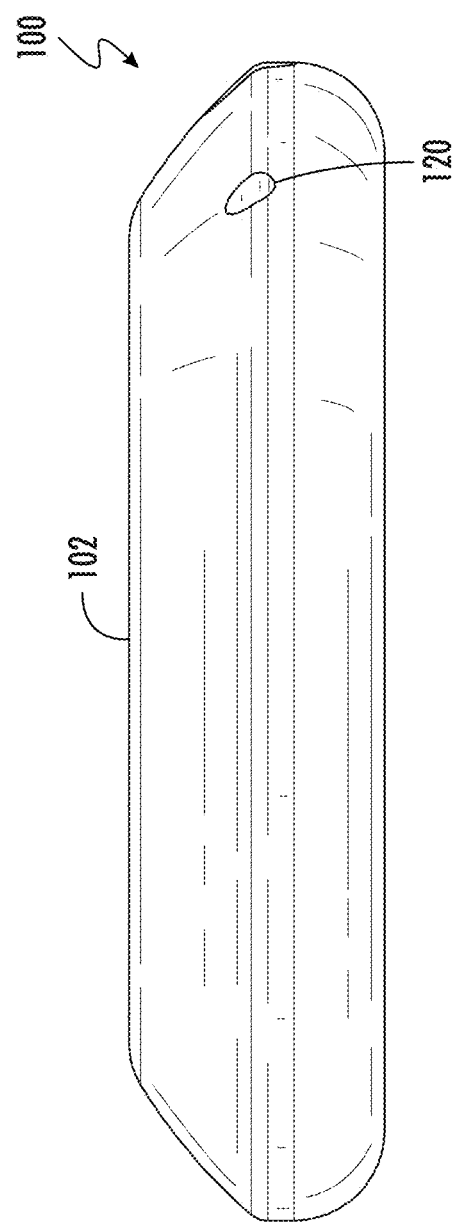
FIG. 7 is a schematic diagram illustrating another side view of the footswitch of FIG. 1A.
Figure 8:
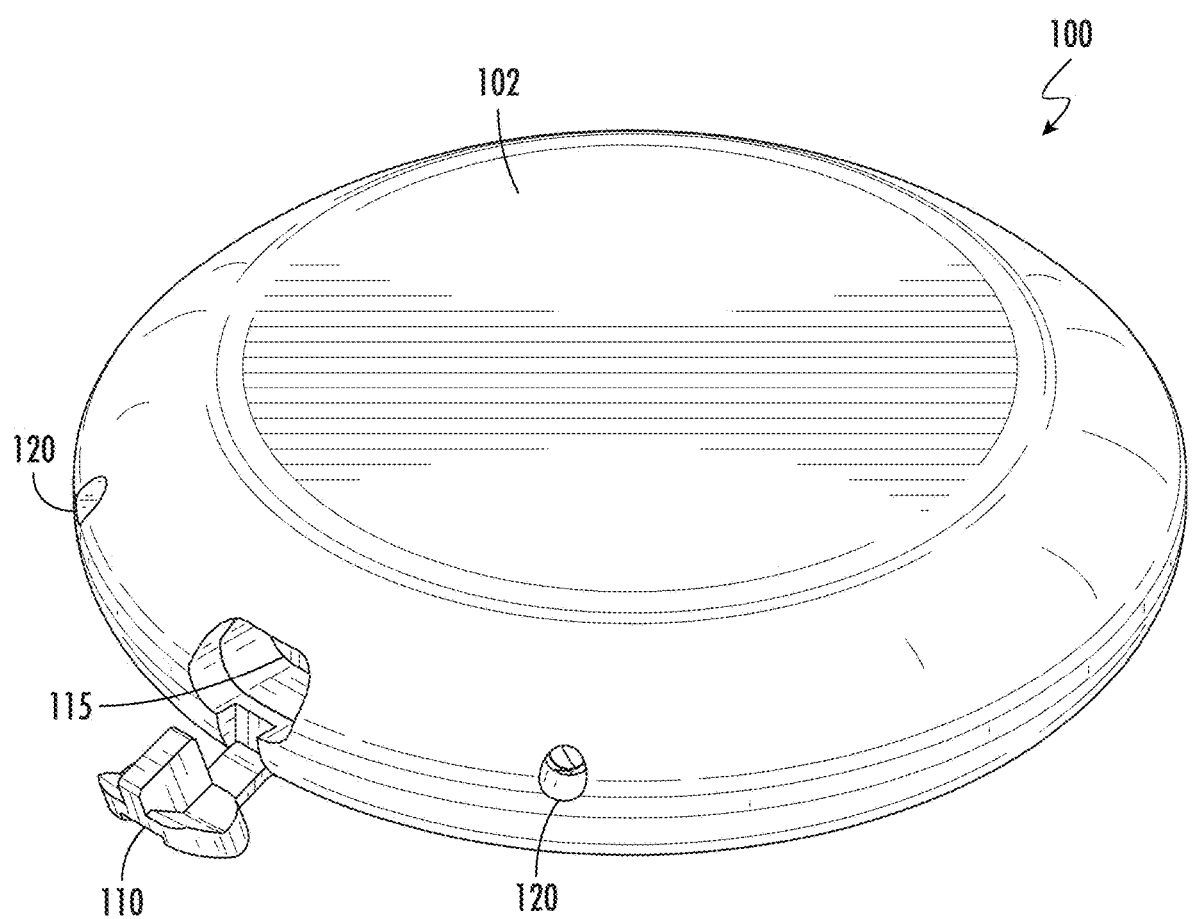
FIG. 8 is a schematic diagram illustrating a front perspective view of the footswitch of FIG. 1A featuring a port.
Figure 9:
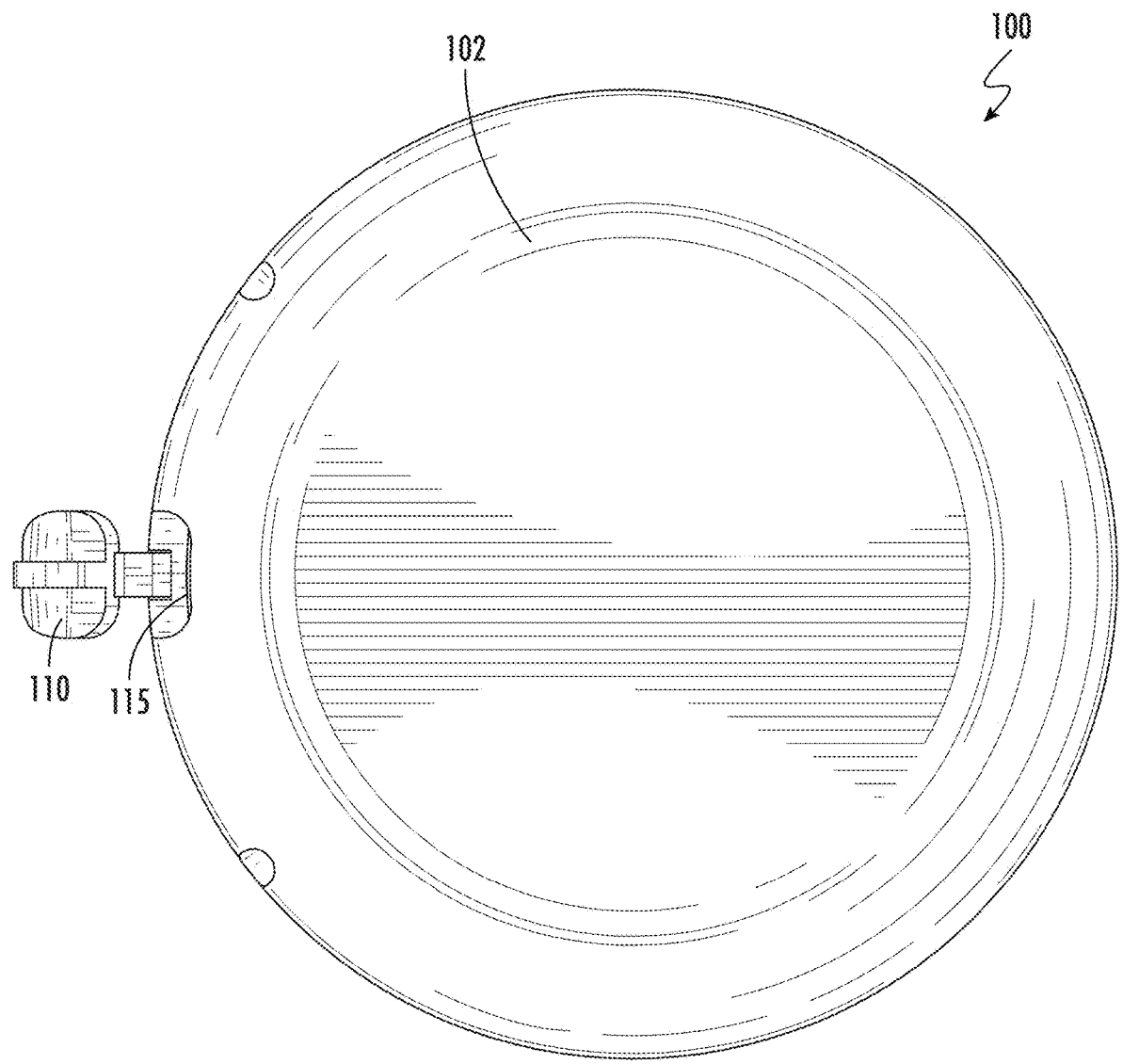
FIG. 9 is a schematic diagram illustrating a top view of the footswitch of FIG. 1A illustrating a port being exposed.
Figure 10:
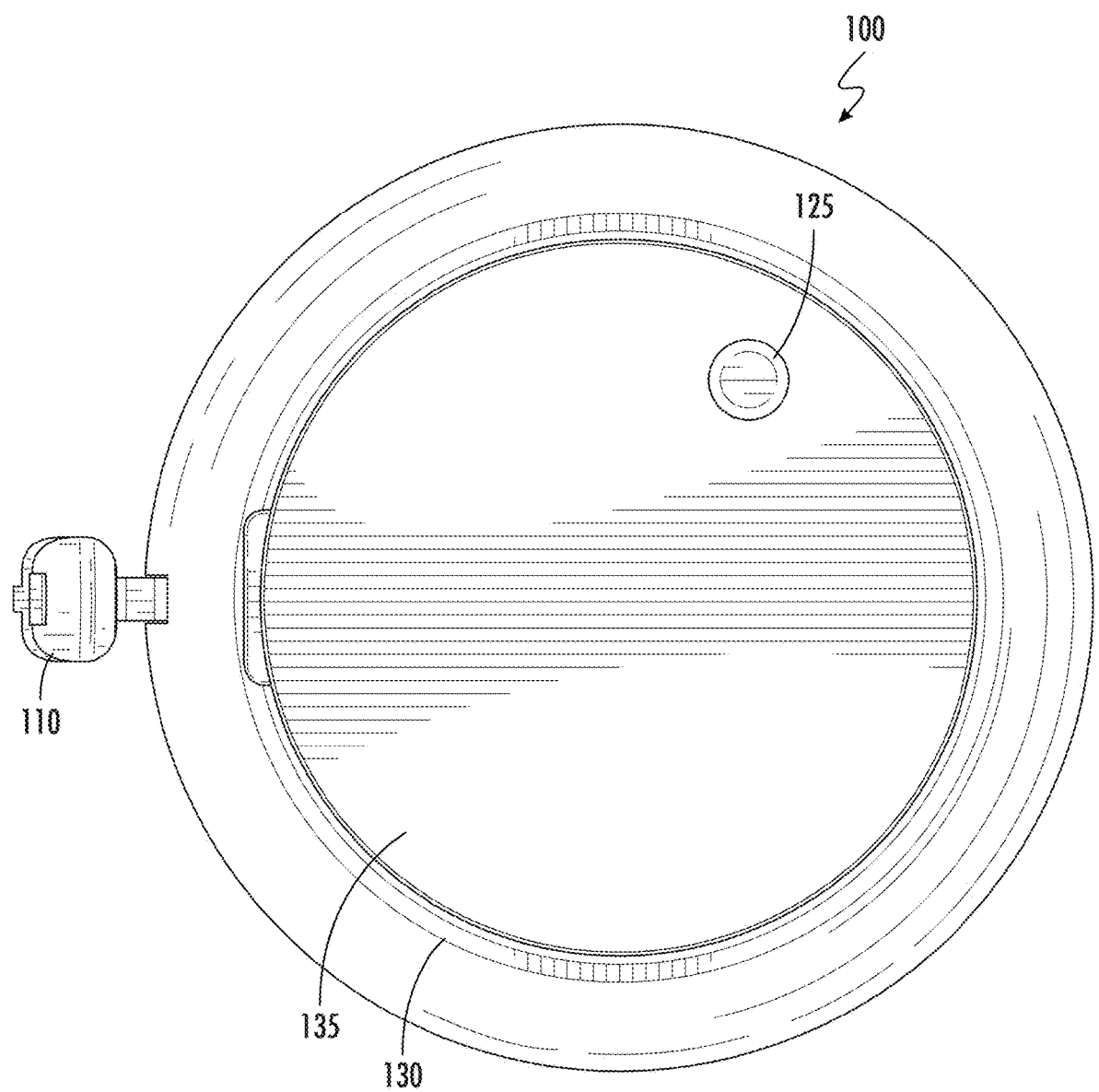
FIG. 10 is a schematic diagram illustrating a bottom view of the footswitch of FIG. 1A.
Figure 11:
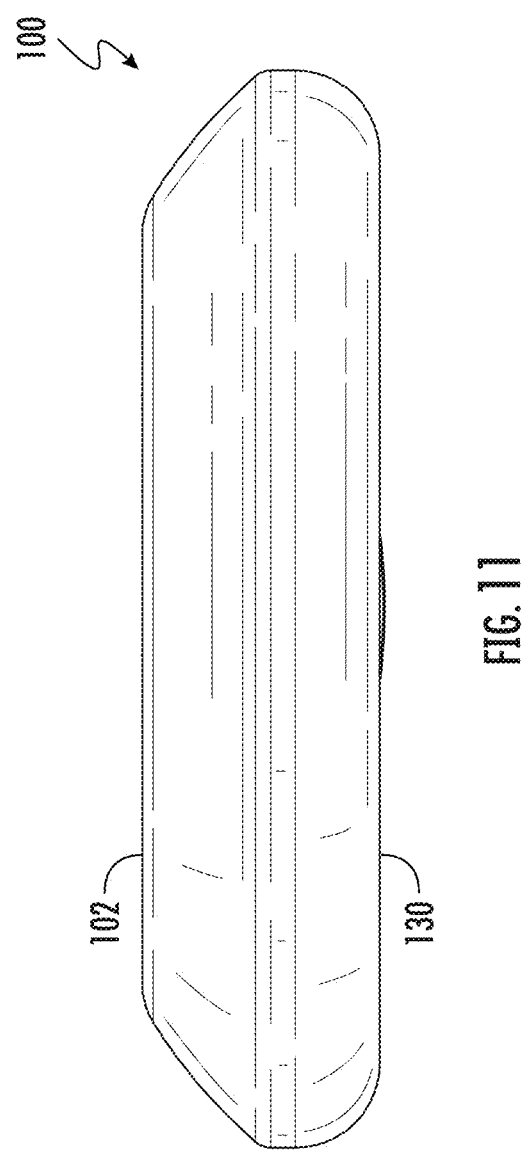
FIG. 11 is a schematic diagram illustrating a side view of the footswitch of FIG. 1A.
Figure 12:
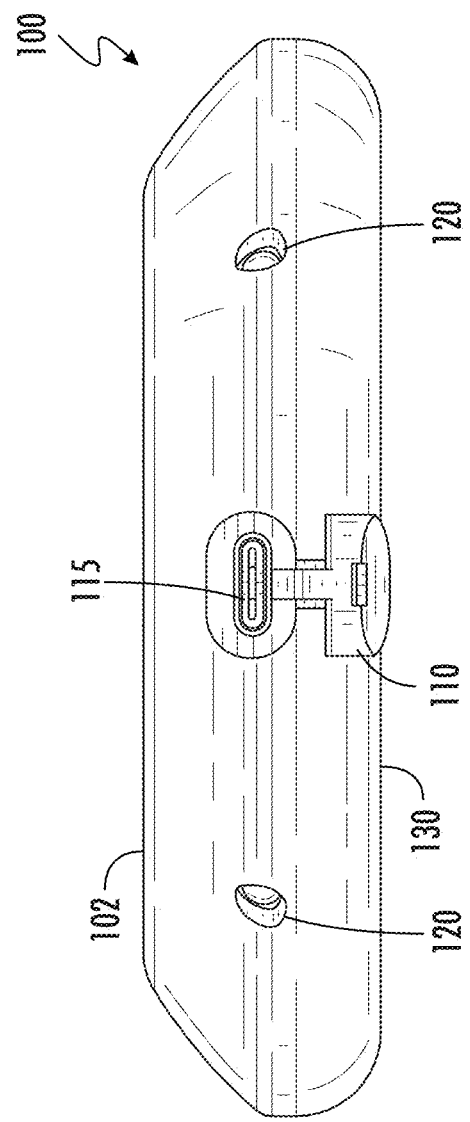
FIG. 12 is a schematic diagram illustrating a side view of the footswitch of FIG. 1A featuring an exposed port.
Figure 13:
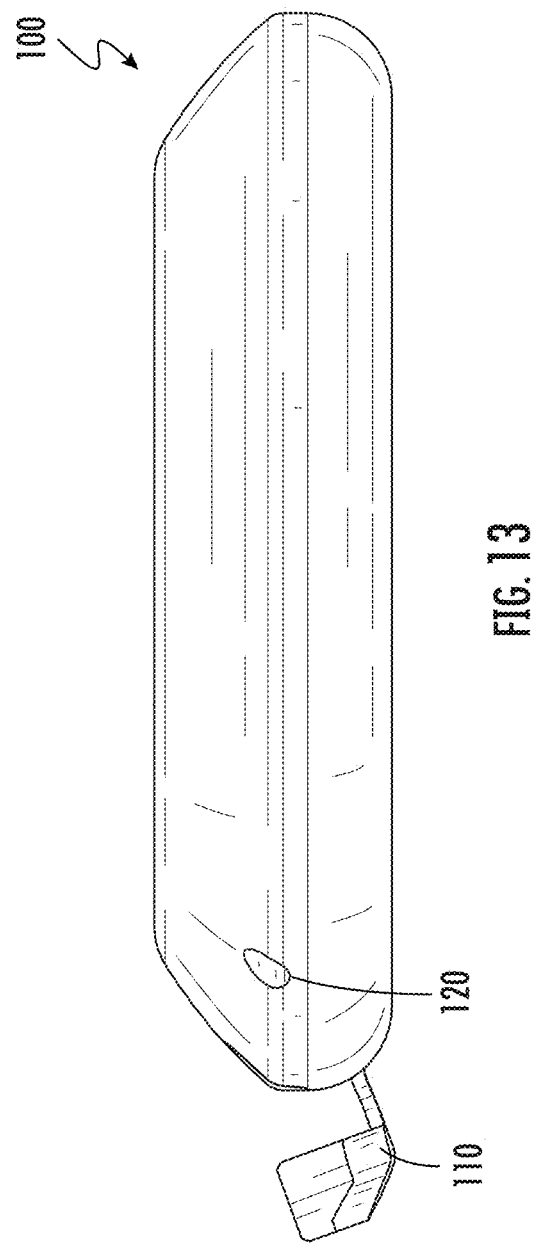
FIG. 13 is a schematic diagram illustrating a side view of the footswitch of FIG. 1A.
Figure 14:
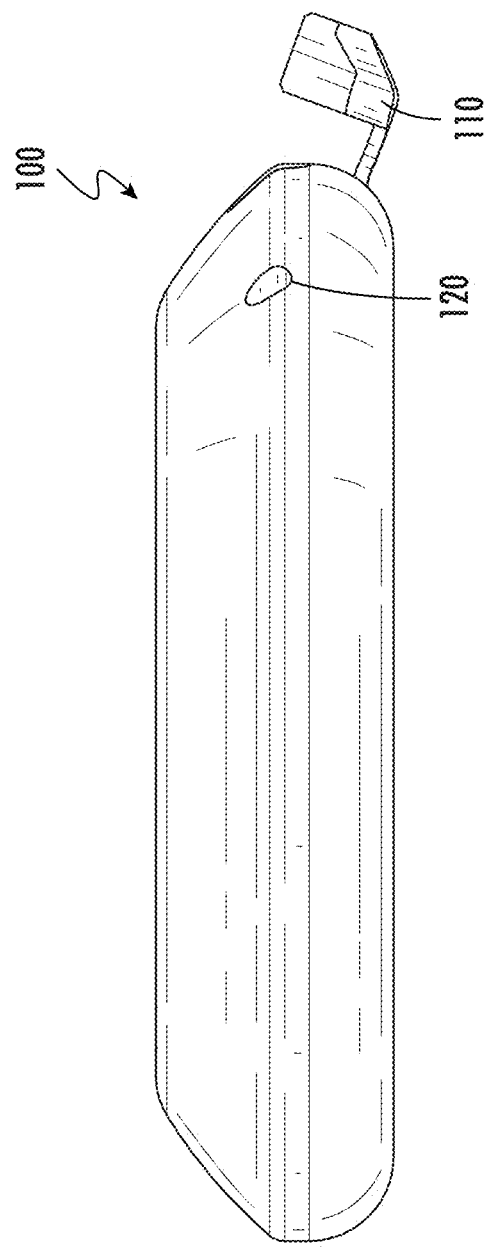
FIG. 14 is a schematic diagram illustrating a side view of the footswitch of FIG. 1A.
Figure 15A:
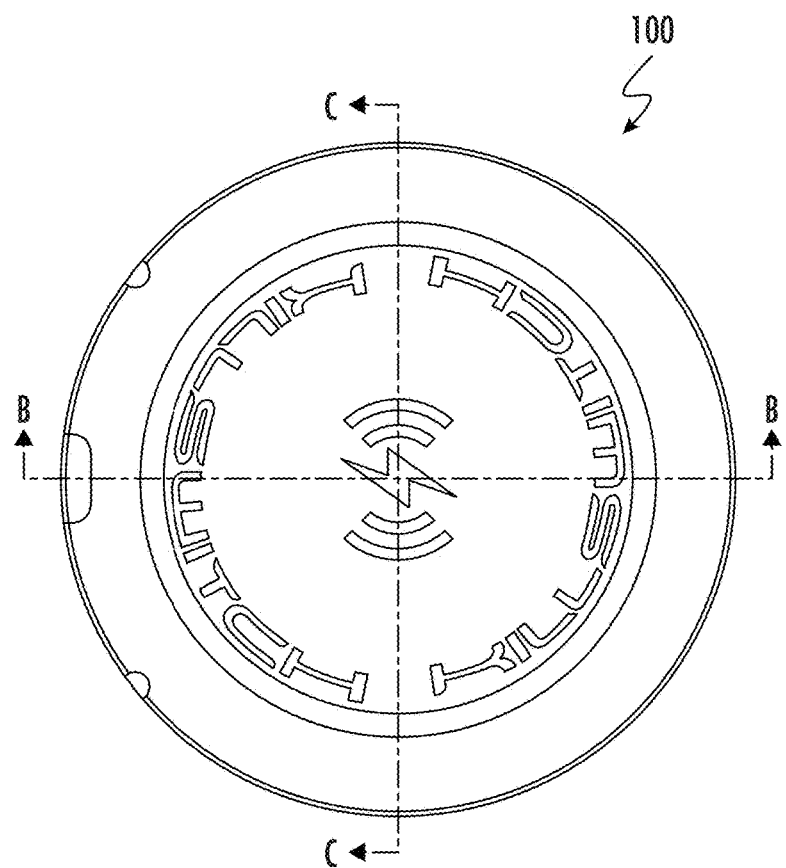
FIG. 15A illustrates a top view a footswitch according to an embodiment of the present disclosure.
Figure 15C:
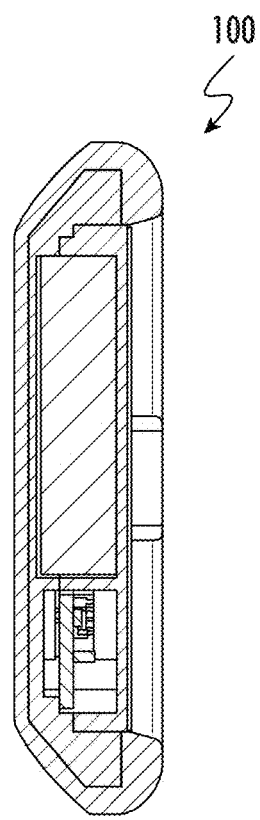
FIG. 15C illustrates a side cross-sectional view of a footswitch according to an embodiment of the present disclosure.
Figure 15B:
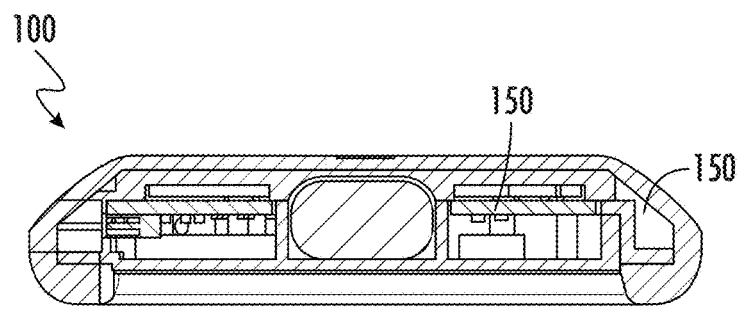
FIG. 15B illustrates a side cross-sectional view of a footswitch according to an embodiment of the present disclosure.
Figure 16A:
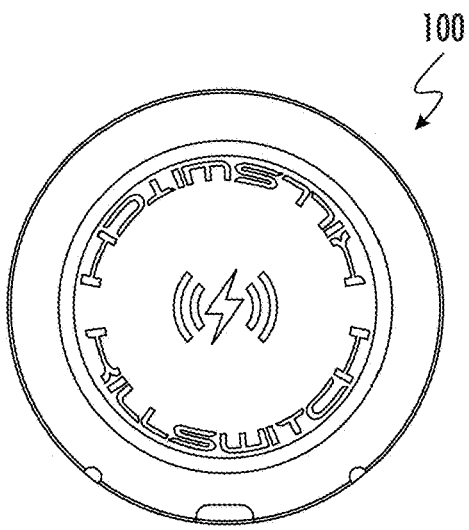
FIGS. 16A, 16B, 16C, 16D, 16E and 16F illustrates top, bottom, and angled perspective views of a footswitch according to an embodiment of the present disclosure.
Figure 16B:
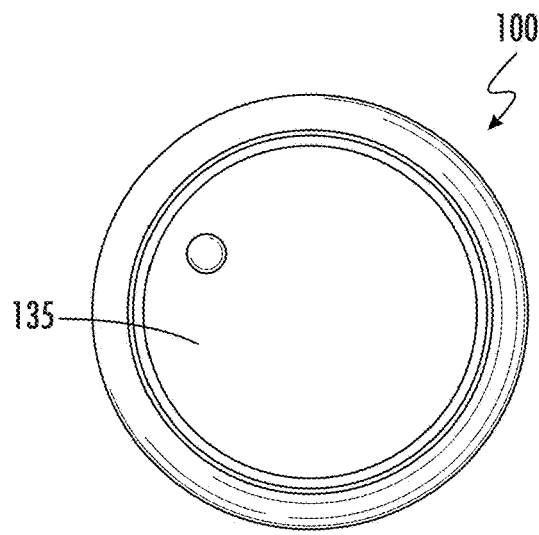
Figure 16C:
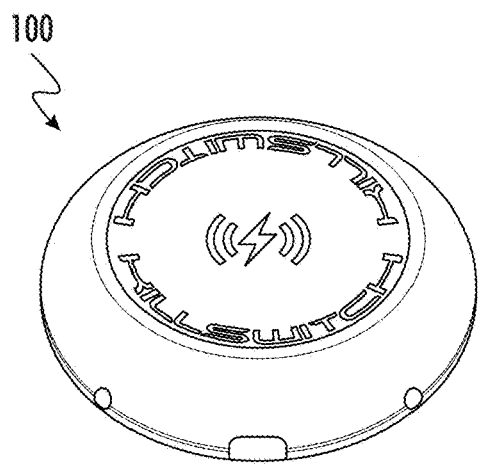
Figure 16D:
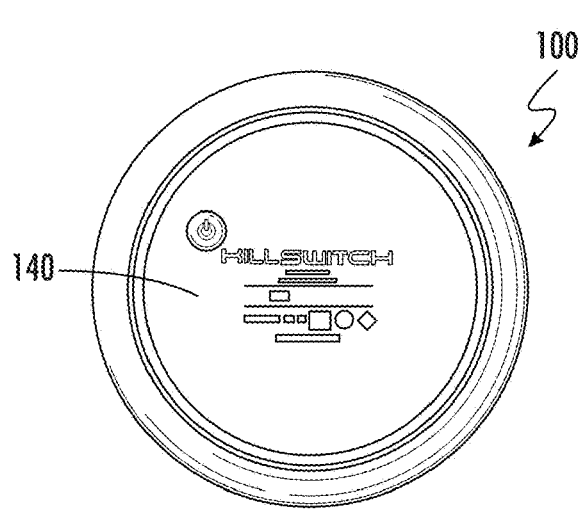
Figure 16E:
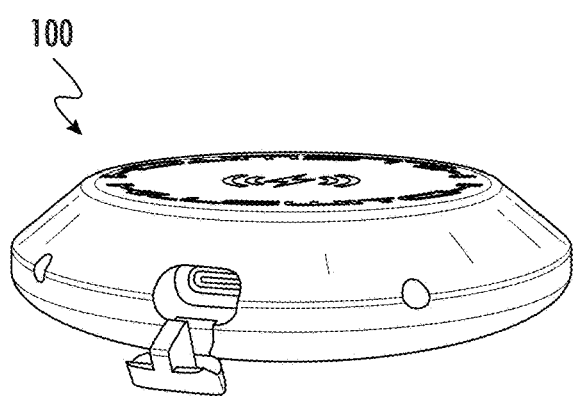
Figure 16F:
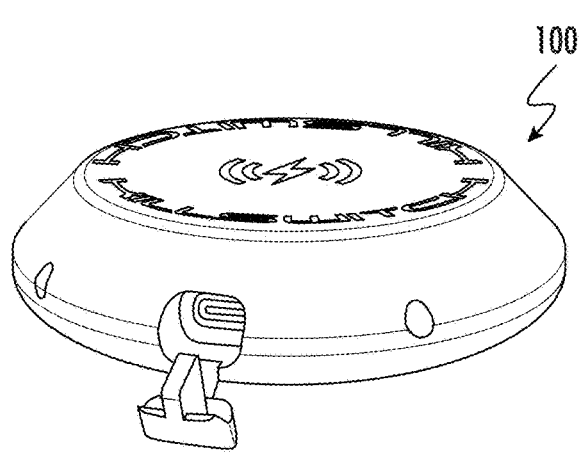

The housing 101 may serve as the outer covering of the footswitch 100 and may be utilized to house the components of the footswitch 100. In certain embodiments, the housing 101 may be made of plastic including overmolded rubber, however, in other embodiments, other housing materials may also be utilized in conjunction with the plastic and rubber and/or as a replacement for the plastic and/or rubber. The housing 101 may protect the components residing in the interior of the footswitch 100, such as from drops and/or from intrusion of substances, such as liquids. In certain embodiments, the housing 101 may have any desired shape, however, in a preferred embodiments, housing 101, which may include a top portion 102 and a bottom portion 130, may be shaped such that a portion of the top portion 102 is flat, but remaining portions of the top portion 102 gradually slope downward beyond the flat portion. The bottom portion 130 may have any desired shape as well, however, in a preferred embodiment, a portion of the bottom portion 130 may be flat and portions of the bottom portion 130 extending beyond the flat portion may gradually slope upward, as is shown in FIG. 4. In certain embodiments, the footing of the housing 101 of the footswitch 100 may be part of the molded shape of the housing 101 to facilitate in the acceleration of the footswitch 100 when tapped on by a user's foot so that the accelerometer 150 detects sudden movements (e.g. taps). In certain embodiments, the housing 101 may also include a plug that may be utilized for sealing the top exterior of the footswitch 101 to prevent substances, such as cleaning agents or other liquids, from getting inside the compartment 180 of the housing 101. In certain embodiments, the housing 101 may also include any number of vents 120, which may be utilized to dissipate and release heat generated by components of the footswitch 100.

The tab 110 of the footswitch 100 may be utilized to cover the port 115, such as when the port 115 is not in use. The port 115 may be exposed when the user positions one or more fingers on the tab 110 and pulls the tab 110 away from the housing 101 of the footswitch 100. Similarly, in order to cover the port 115, the user may push the tab 110 back into place so that the tab 110 is flush with the exterior surface of the housing 101. The port 115 may be any type of port, such as a communications port, charging port, any type of port, or a combination thereof. In a preferred embodiment, the port 115 may be a charging port, which may be configured to connect with a cable (e.g. USB cable), which may be configured to deliver power to the footswitch 100 when the other end of the cable is connected to a power source. In certain embodiments, data, signals, and/or information from the components of the footswitch 100 may be transmitted via the port 115, through the cable, and then to another device.

As indicated herein, the footswitch 100 may also include a bottom lid 135. The bottom lid 135 may be made of plastic and/or any other suitable material. In certain embodiments, the bottom lid 135 may be bolted down against the housing 101 using screws and/or other fastening mechanisms. In certain embodiments, the bottom lid 135 may include an opening 124 through which the power switch 125 of the footswitch 100 may protrude so that the power switch 125 is readily accessible to a user of the footswitch 100. The power switch 125 may be utilized to turn the footswitch 100 on or off. The radio frequency ground plate and overlay membrane 140 may be utilized to cover the bottom lid 135, the screws (or other fastening mechanisms), and/or the power switch 125. In certain embodiments, the membrane 140 may be configured to rest on top of or above the bottom lid 135 when the bottom lid 135 is secured to the housing 101. In certain embodiments, the membrane 140 may be within the housing 101. In certain embodiments, the membrane 140 may be configured to be positioned on any location on the housing 101 and/or the footswitch 100. In certain embodiments, the membrane 140 may be made of polyethylene terephthalate (PET) and/or copper film. In certain embodiments, the membrane 140 may be embossed, covered, and/or printed with graphics and/or designs, as shown in FIGS. 16A, 16B, 16C, 16D, 16E, and 16F. For example, the membrane 140 may include graphics for the power switch 125 and a convex surface around the power switch 125, which may be pressed by the user. The copper film of the membrane 140 may serve as a shield to reflect radio frequency (or other) signals transmitted by the communication device 155 so that the signals emit upwards towards a tattoo machine 200 paired with the footswitch 100. As a result, the copper film may prevent or reduce such signals from contacting and absorbing into the floor (or surface beneath the footswitch 100), which may generate a lag in signal connection between the footswitch 100 and the tattoo machine 200. In certain embodiments, the membrane 140 may also act as a nameplate overlay that may display compliance information, a serial number, product name, and/or any other desired information.

In certain embodiments, the footswitch 100 may include any number of magnets 141. The magnets 141 may have any desired strength, shape, configuration, or a combination thereof. For example, the magnets 141 may be round in shape, rectangular in shape, and/or have any shape. In certain embodiments, any number of magnets 141 may be utilized and/or secured to the footswitch 100 and/or tattoo machine 200. For instance, one or more magnets can be located in the foot or bottom ridge of the footswitch 100 or the entire ridge can be a magnet 141. The magnets 141 may be utilized to secure the footswitch to a surface so that the footswitch 100 remains in a fixed position and is secured in place. For example, the magnets 141 may be utilized to place the footswitch 100 on a metal surface so that when a tattoo artist is using the footswitch 100, the footswitch 100 does not move away from the tattoo artist's general vicinity. As another example, the magnets 141 may be utilized the place the switch 100 on a metal surface, such as a portion of a chair, for use by the user's hand instead of their foot. The magnets 141 may also be utilized to secure the footswitch 100 to the tattoo machine 200, to another device, to an accessory of the tattoo machine 200 and/or footswitch 100, or a combination thereof.

The accelerometer 150 of the footswitch 100 may reside within the housing 101 and may be configured to measure any type of acceleration with respect to the footswitch 100. For example, the accelerometer 150 may be configured to measure accelerations and/or changes in acceleration occurring on a surface of the housing 101, on any surface of the footswitch 100, or a combination thereof. An action that may amount to acceleration may include, but is not limited to, a tap on the housing 101 surface, a pattern of taps, any type of contact with the housing 101 and/or other components of the footswitch 100, a slide movement on a surface of the footswitch 100, any motion with respect to a surface of the footswitch 100, or a combination thereof. The accelerometer 150 may include any components of a traditional accelerometer and may be configured to generate signals based on detection of the accelerations. In certain embodiments, the accelerometer 150 may be paired with a gyroscope and/or include gyroscope functionality so as to detect orientational movements and/or other movements as well. In certain embodiments, the type of signal generated may be based on the type of acceleration, the pattern of acceleration, the length of the acceleration, the speed of the acceleration, any metric associated with acceleration, a rate of increase or decrease of the acceleration, or a combination thereof. The type of signal may dictate the type of action to be performed with respect to the tattoo machine 200 and/or the footswitch 100 itself. For example, the signal generated may be utilized to activate or deactivate a tattoo machine 200 paired with the footswitch 100, adjust a setting of the tattoo machine 200 (e.g. voltage level, give level, LED brightness of a LED of the tattoo machine 200, audio levels for audio outputted by the tattoo machine 200, reprogram an input device of the tattoo machine to have different functionality, any other setting of the tattoo machine 200, or a combination thereof), perform an operation of the tattoo machine 200 (e.g. provide power to a motor of the tattoo machine 200, adjust a needle speed of a needle connected to the tattoo machine 200, adjust a type of motion for the needle of the tattoo machine 200, deactivate or reactivate the tattoo machine 200 after a certain period of time, perform any tattoo machine operation, activate and/or deactivate the footswitch 100, control operation of the footswitch 100, adjust a setting of the footswitch 100, or a combination thereof.

The footswitch 100 may also include a communication device 155. The communication device 155 may be a device and/or software that may be utilized to transmit and/or receive signals from and/or to the footswitch 100 and/or tattoo machine 200. In certain embodiments, the communication device 155 may be a short-range wireless chip (e.g. Bluetooth, etc.), a transceiver, a long-range chip, a cellular chip, a radio frequency device, an Internet of Things (IoT) device, a near-field communications chip, any type of communication device and/or software, or a combination thereof. In certain embodiments, the communication device 155 may be configured to facilitate communication via Bluetooth connectivity, ZigBee, Z-wave, any type of wireless protocol, radio technologies, cellular technologies, satellite technologies, mesh technologies, infrared technologies, any other communication technologies, or a combination thereof. In certain embodiments, the communication device 155 may include an embedded microprocessor and/or memory. The communication device 155 may be configured to receive signals from the accelerometer 150, process the signals, and then transmit the signals to the tattoo machine 200, such as via a communication device of the tattoo machine 200. Such signals may be utilized to activate or deactivate the tattoo machine 200, control operation of the tattoo machine 200, adjust settings of the tattoo machine 200, perform any action with respect to the tattoo machine 200, or a combination thereof. The communication device 155 may also be configured to receive signals from the tattoo machine 200, such as via a communication device of the tattoo machine 200. Such signals received from the tattoo machine may be utilized to provide information about the tattoo machine 200 to the footswitch 100 (e.g. sensor data, data associated with the components of the tattoo machine 200, data associated with how the tattoo machine 200 is operating, any other data, data associated with power levels, data associated with battery life, data associated with needle reciprocation of a needle of the tattoo machine 200, data associated with operation of a motor of the tattoo machine 200, or a combination thereof), optionally provide control instructions for controlling the footswitch 100, provide any other information, or a combination thereof.

The footswitch 100 may also include a battery 160. The battery 160 may be any type of battery including a traditional battery, a rechargeable battery, any other type of battery, or a combination thereof. The battery 160 may be utilized to power the footswitch 100, such as when the footswitch 100 is not obtaining power via a power cable connected to the port 115. The battery 160 may be charged by utilizing battery charger circuit 165, which may be configured to charge when the power cable is providing power to the footswitch 100. The battery charger circuit 165 may also be utilized to regulate power to the accelerometer 150, the communication device 155, and/or to any other components of the footswitch 100. In certain embodiments, the footswitch 100 may also include any number of processors 170, memories 175, and/or any other components as well.

Notably, the footswitch 100 described herein avoids having to use a mechanical switch, which limits the angle at which a footswitch can be activated by a user, such as by using the user's foot. The accelerometer 150 allows the user to activate the footswitch 100 and/or control the tattoo machine 200 at any angle, position, and/or location on the surface of the footswitch 100. In certain embodiments, to further enhance radio frequency reception (or other types of reception) of the footswitch 100, an external antenna may be added to the communication device 150. In certain embodiments, the communication device may include two antennas or a greater number of antennas and may include high gain antennas. Additionally, tuning capacitors may also be utilized with the footswitch 100 as well. In certain embodiments, the output power for the footswitch 100 may be set to 8 dB, however, other dB levels may also be utilized. In certain embodiments, the housing 101 material may be plastic in order to enhance radio frequency connectivity of the footswitch 100. In certain embodiments, the footswitch 100 may be activated in any desired fashion. For example, a user may place the footswitch 100 on a floor or a table, and the footswitch 100 may be activated by tapping on an adjacent surface. In certain embodiments, the footswitch 100 may also include a user interface, which may be a touchscreen or other interface, and may be utilized to receive inputs and/or commands from a user. In certain embodiments, the footswitch 100 may also include voice detection technology to process voice commands for controlling the footswitch 100 operation as well. Notably, the footswitch 100 may also be utilized with other accessories of a tattoo machine 200. For example, the footswitch 100 may be utilized with wireless battery packs, portions of a tattoo machine 200, controllers for controlling the tattoo machine 200, wired battery packs, any tattoo machine accessory, or a combination thereof.

The tattoo machine 200 may be utilized to apply tattoo ink onto the skin of a tattoo recipient, such as a person. In certain embodiments, the tattoo machine 100 may include any number components, including, but not limited to, battery packs, needle cartridges including tattoo needles, motors, communication devices, processors, memories, user interfaces, controls, any other components, or a combination thereof. In certain embodiments, the tattoo machine 200 may include a grip that a tattoo artist may grip while utilizing the tattoo machine 200. Additionally, a motor of the tattoo machine 200 may be utilized to power and actuate the various components of the tattoo machine 200. The footswitch 100 may be utilized to control the operation of the tattoo machine 200, such as by transmitting signals from the accelerometer 150 to the tattoo machine 200 that are generated based on accelerations detected on the surface of the housing 101 of the footswitch 100 and/or other accelerations detected by the footswitch 100.

Although FIGS. 1-16 illustrates specific example configurations of the footswitch 100 and tattoo machine 200, these devices may include any configuration of the components, which may include using a greater or lesser number of the components. For example, the footswitch 100, the tattoo machine 200, and/or any of the other components shown in FIGS. 1-16 may include any number of memories, processors, housings 101, tabs 110, bottom lids 135, membranes 140, accelerometers 150, communication devices 155, batteries 160, battery charger circuits 165, buttons, controls, and/or other components. Additionally, the footswitch 100 may also serve as an intermediary device for controlling the tattoo machine 200. For example, instead of directly transmitting signals to a communication device of the tattoo machine 200, the footswitch may transmit control signals to an intermediary device, such as a computer or other device, which may forward the control signals to the tattoo machine 200.

Figure 17:
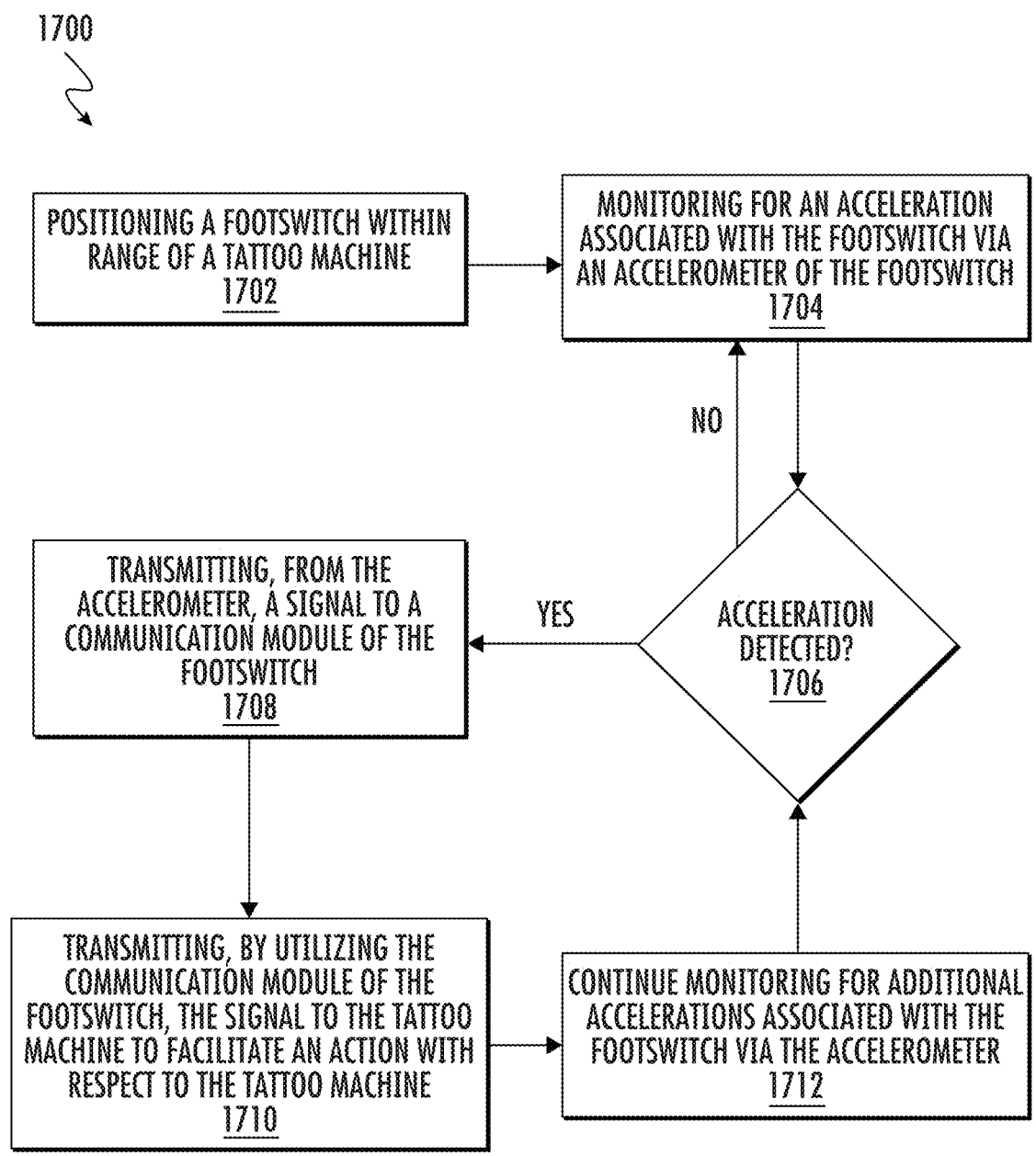
FIG. 17 is a flow diagram illustrating a sample method for utilize a footswitch with a tattoo machine according to an embodiment of the present disclosure.

Notably, as shown in FIG. 17, an exemplary method 1700 for utilizing a footswitch (e.g. footswitch 100) with a tattoo machine (e.g. tattoo machine 200) is schematically illustrated. The method 1700 may include, at step 1702, positioning a footswitch (e.g. footswitch 100) within range of a tattoo machine (e.g. tattoo machine 200). In certain embodiments, within range may include, but is not limited to, a communication range, a specified minimum distance, a specified maximum distance, or a combination thereof. At step 1704, the method 1700 may include monitoring for an acceleration associated with the footswitch via an accelerometer (e.g. accelerometer 150) of the footswitch. An acceleration may include, but is not limited to, a tap on the housing 101 of the footswitch, contact with the housing 101 of the footswitch, a slide across a surface of the footswitch, a pattern of contacts with the footswitch, At step 1706, the method 1700 may include determining whether an acceleration has been detected by the accelerometer of the footswitch. If an acceleration has not been detected, the method 1700 may revert back to step 1704 and continue to monitor for accelerations associated with the footswitch. If, however, at step 1706, an acceleration is detected, the method 1700 may proceed to step 1708.

At step 1708, the method 1700 may include generating a signal and transmitting, from the accelerometer, the signal to a communication device of the footswitch. The signal may be generated based on the specific type and/or pattern of acceleration(s) detected by the accelerometer and may be utilized to facilitate actions with respect to the tattoo machine. Once the signal is provided to the communication device of the footswitch, the method 1700 may proceed to step 1710. At step 1710, the method 1700 may include transmitting, by utilizing the communication device, the signal to the tattoo machine. For example, the signal may be transmitted from the communication device of the footswitch to a communication device of the tattoo machine. Once the signal is received by the tattoo machine, the signal may be utilized to facilitate any number of actions with respect to the tattoo machine. For example, the signal may be utilized to activate the tattoo machine, deactivate the tattoo machine, adjust a setting associated with the tattoo machine, control the tattoo machine, and/or perform any other operations associated with the tattoo machine. The settings may include, but are not limited to, a brightness level of a user interface of the tattoo machine, a voltage setting of the tattoo machine, an electronic give level for controlling the operation of a needle of a needle cartridge of the tattoo machine (e.g. to adjust the needle strike onto the skin of a user from hard to soft), a power level of the tattoo machine, any other setting associated with the tattoo machine, or a combination thereof. Operations of the tattoo machine may include any operation that the tattoo machine may perform. For example, an operation may include adjusting a rate at which a needle of the tattoo machine moves, stopping movement of the needle of the tattoo machine, initiating movement of the needle of the tattoo machine, causing the tattoo machine to go into a wait mode, causing the tattoo machine alter a type of movement of the needle, unpair or pair the tattoo machine and the footswitch, obtain sensor data from sensors of the tattoo machine, obtain any data associate with the tattoo machine, perform any other operation, or a combination thereof. At step 1712, the method 1700 may continue to monitor for additional accelerations associated with the footswitch by utilizing the accelerometer. As additional accelerations are detected, the method 1700 may revert back to step 1706 and continue accordingly. Notably, the method 1700 may further incorporate any of the features and functionality described herein.

Referring now also to FIG. 18, at least a portion of the methodologies and techniques described with respect to the exemplary embodiments of the switch 100 can incorporate a machine, such as, but not limited to, computer system 1800, or other computing device within which a set of instructions, when executed, may cause the machine to perform any one or more of the methodologies or functions discussed above. The machine may be configured to facilitate various operations conducted by the switch 100. For example, the machine may be configured to, but is not limited to, assist the switch 100 by providing processing power to assist with processing loads experienced in the switch 100, by providing storage capacity for storing instructions or data traversing the switch 100 and/or tattoo machine 200, or by assisting with any other operations conducted by or within the switch 100. As another example, the computer system 1800 may assist with detecting accelerations on the housing 101, generating signals in response to the detected accelerations, transmitting the signals to the communication device 155, transmitting signals to the tattoo machine 200, and/or performing any operation described herein.

In some embodiments, the machine may operate as a standalone device. In some embodiments, the machine may be connected (e.g., using a communications network 135, another network, or a combination thereof) to and assist with operations performed by other machines and systems, such as, but not limited to, the switch 100, the tattoo machine 200, any other system, program, and/or device, or any combination thereof. The machine may be connected with any component of the switch 100, the tattoo machine 200, or a combination thereof. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 1800 may include a processor 1802 (e.g., a central processing unit (CPU), a graphics processing unit (GPU, or both), a main memory 1804 and a static memory 1806, which communicate with each other via a bus 1808. The computer system 1800 may further include a video display unit 1810, which may be, but is not limited to, a liquid crystal display (LCD), a flat panel, a solid state display, or a cathode ray tube (CRT). The computer system 1800 may include an input device 1812, such as, but not limited to, a keyboard, a cursor control device 1814, such as, but not limited to, a mouse, a disk drive unit 1816, a signal generation device 1818, such as, but not limited to, a speaker or remote control, and a network interface device 1820.

The disk drive unit 1816 may include a machine-readable medium 1822 on which is stored one or more sets of instructions 1824, such as, but not limited to, software embodying any one or more of the methodologies or functions described herein, including those methods illustrated above. The instructions 1824 may also reside, completely or at least partially, within the main memory 1804, the static memory 1806, or within the processor 1802, or a combination thereof, during execution thereof by the computer system 1800. The main memory 1804 and the processor 1802 also may constitute machine-readable media.

In certain embodiments, the machine may also include the accelerometer 150, the communication device 155, the battery 160, the battery charger circuit 165, the processor 170, and/or the memory 175. The machine may be configured to reside within the footswitch 100, the tattoo machine 200, both the footswitch 100 and tattoo machine 200, as a standalone machine, and/or in other devices.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware devices or devices with related control and data signals communicated between and through the devices, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 1822 containing instructions 1824 so that a device connected to the communications network 135, another network, or a combination thereof, can send or receive voice, video or data, and communicate over the communications network 135, another network, or a combination thereof, using the instructions. The instructions 1824 may further be transmitted or received over the communications network 135, another network, or a combination thereof, via the network interface device 1820.

While the machine-readable medium 1822 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other rewritable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the disclosure. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this disclosure, but that the disclosure will include all embodiments and arrangements falling within the scope of the appended claims.

The foregoing is provided for purposes of illustrating, explaining, and describing embodiments of this disclosure. Modifications and adaptations to these embodiments will be apparent to those skilled in the art and may be made without departing from the scope or spirit of this disclosure. Upon reviewing the aforementioned embodiments, it would be evident to an artisan with ordinary skill in the art that said embodiments can be modified, reduced, or enhanced without departing from the scope and spirit of the claims described below.

We claim:

1. A tattoo machine system, the system comprising:
    a tattoo machine; and
    a switch or footswitch configured to communicatively link with the tattoo machine, the switch or footswitch comprising:
        a housing;
        an accelerometer within the housing configured to detect a change in acceleration associated with the switch or footswitch and generate a signal based on the detected change in acceleration; and
        a communication device configured to receive the signal from the accelerometer upon detection of the change in acceleration associated with the switch or footswitch, wherein the communication device is configured to transmit the signal to the tattoo machine,
    wherein the signal is configured to adjust an electronic give level of a needle of the tattoo machine based on the detected change in acceleration;
    wherein adjusting the give level of the needle further comprises changing a hardness or softness of a needle strike of the needle based on the detected change in acceleration.

2. The tattoo machine system of claim 1, wherein the switch or footswitch further comprises a battery charger circuit configured to charge and regulate power for the accelerometer and the communication device.

3. The tattoo machine system of claim 1, wherein the switch or footswitch further comprises a radio frequency ground plate and overlay membrane for enhancing radio frequency reception for the communication device.

4. The tattoo machine system of claim 1, wherein the switch or footswitch further comprises a rechargeable battery that stores and provides power to the footswitch.

5. The tattoo machine system of claim 1, wherein the switch or footswitch further comprises a port configured to connect with a power cable for powering the footswitch.

6. The tattoo machine system of claim 1, wherein the housing comprises overmolded rubber and a plug for sealing an exterior of the switch or footswitch.

7. The tattoo machine system of claim 1, wherein a top portion of the housing gradually tapers downwards to facilitate flowing of a fluid away from the footswitch when the fluid is poured onto the housing of the switch or footswitch.

8. The tattoo machine system of claim 1, wherein the communication device comprises an external antenna, a tuning capacitor, or a combination thereof.

9. The tattoo machine system of claim 1, wherein the accelerometer is further configured to detect a change in a pattern of acceleration, a length of the acceleration, a speed of acceleration, a rate of increase or decrease of the acceleration, or a combination thereof on any surface of the switch or footswitch;
    wherein the signal generated by the accelerometer is based on the detected change in the pattern of acceleration, the detected change in the length of the acceleration, the detected change in the speed of acceleration, the detected change in the rate of increase or decrease of the acceleration, or a combination thereof.

10. The tattoo machine system of claim 9, wherein the signal is further configured to adjust a voltage of the tattoo machine, adjust a setting of the tattoo machine, or a combination thereof based on the detected change in the pattern of acceleration, the detected change in the length of the acceleration, the detected change in the speed of acceleration, the detected change in the rate of increase or decrease of the acceleration, or a combination thereof.

11. The tattoo machine system of claim 1, wherein the switch or footswitch comprises a bottom lid configured to be attached to a base of the housing.

12. The tattoo machine system of claim 11, wherein the bottom lid includes an opening through which a power switch of the switch or footswitch is configured to protrude.

13. The tattoo machine system of claim 12, wherein the switch or footswitch further comprises a membrane for sealing over at least a portion of the bottom lid.

14. A method, comprising:
    positioning a switch or footswitch within range of a tattoo machine;
    detecting a change in acceleration associated with the switch or footswitch via an accelerometer of the footswitch;
    transmitting, based on the detected change in acceleration, a signal from the accelerometer to a communication device of the switch or footswitch;
    transmitting, by utilizing the communication device, the signal to the tattoo machine; and
    adjusting, based on the transmitted signal, an electronic give level of a needle of the tattoo machine, wherein adjusting the electronic give level of the needle further comprises adjusting a hardness or softness of a needle strike of the needle based on the detected change in acceleration.

15. The method of claim 14, further comprising facilitating reflection of the signal towards the tattoo machine by utilizing a radio frequency ground plate and overlay membrane of the footswitch.

16. The method of claim 14, further comprising detecting another acceleration, and further comprising transmitting a different signal from the accelerometer based on the another acceleration.

17. The method of claim 14, wherein detecting the change in acceleration associated with the switch or footswitch further comprises detecting a change in a pattern of acceleration, a length of the acceleration, a speed of acceleration, a rate of increase or decrease of the acceleration, or a combination thereof on any surface of the footswitch.

18. A footswitch, comprising:
    a housing;

an accelerometer within the housing configured to detect a change in acceleration associated with the switch or footswitch; and a communication device configured to receive a signal from the accelerometer upon detection of the change in acceleration associated with the switch or footswitch, and wherein the communication device is configured to transmit the signal to a tattoo machine, wherein the signal is configured to adjust an electronic give level of a needle of the tattoo machine based on the detected change in acceleration, wherein adjusting the give level further comprises changing a hardness or softness of a needle strike of the needle based on the detected change in acceleration.

19. The method of claim 17, wherein the method further comprises adjusting a voltage of the tattoo machine, adjusting a setting of the tattoo machine, or a combination thereof based on the detected change in the pattern of acceleration, the detected change in the length of the acceleration, the detected change in the speed of acceleration, the detected change in the rate of increase or decrease of the acceleration, or a combination thereof.

\* \* \* \* \*